United States Patent
Lavedan et al.

(10) Patent No.: US 9,458,507 B1
(45) Date of Patent: Oct. 4, 2016

(54) ANTIPSYCHOTIC TREATMENT BASED ON SNP GENOTYPE

(71) Applicant: Vanda Pharmaceuticals, Inc., Washington, DC (US)

(72) Inventors: Christian Lavedan, Potomac, MD (US); Simona Volpi, Derwood, MD (US); Louis Licamele, Potomac, MD (US); Mihael H. Polymeropoulos, Potomac, MD (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 0 days.

(21) Appl. No.: 15/085,778

(22) Filed: Mar. 30, 2016

Related U.S. Application Data (63) Continuation of application No. 12/675,598, filed as application No. PCT/US2008/075845 on Sep. 10, 2008, now Pat. No. 9,328,387.

(60) Provisional application No. 60/971,227, filed on Sep. 10, 2007, provisional application No. 61/018,584, filed on Jan. 2, 2008.

(51) Int. Cl.
 *C12Q 1/68* (2006.01)
 *A61K 31/454* (2006.01)

(52) U.S. Cl.
 CPC ........... *C12Q 1/6883* (2013.01); *A61K 31/454* (2013.01); *C12Q 2600/106* (2013.01); *C12Q 2600/156* (2013.01)

(58) Field of Classification Search
 None
 See application file for complete search history.

(56) References Cited

U.S. PATENT DOCUMENTS

| 5,474,796 A | 12/1995 | Brennan |
| 2006/0073506 A1 | 4/2006 | Christians et al. |

FOREIGN PATENT DOCUMENTS

| WO | 03054226 A2 | 7/2003 |
| WO | 2006039663 A2 | 4/2006 |
| WO | 2008144599 A2 | 11/2008 |

OTHER PUBLICATIONS

Patent Cooperation Treaty, PCT Notification of Transmittal of The International Search Report and The Written Opinion of the International Searching Authority, or the Declaration, dated Feb. 24, 2009 for Application No. PCT/US2008/075845, filed Sep. 10, 2008, 23 pages.
Jain, "An Assessment of Iloperidone for the Treatment of Schizophrenia", Dec. 2000, pp. 2935-2943, KP008092743, Ashley Publications Ltd., ISSN: 1354-3784, London, GB.
Kelleher et al., "Advances in Atypical Antipsychotics for the Treatment of Schizophrenia: New Formulations and New Agents", pp. 249-261, XP-001079584, CNS Drugs 2002, vol. 16, No. 4, ADIS International, Auckland, NZ.
NCBI, Probe: Reagents for Functional Genomics, 2006, 1 page, XP-002503745, "Sequence-specific oligonucleotide (SSO) probe for Homo sapiens variation rs11851892", Probe Pr005074415.
NCBI, Probe: Reagents for Functional Genomics, 2007, 1 page, XP-002503744, "Bead microarray element (bead) probe for Homo sapiens variation rs11851892", Probe Pr008160271.
Pickard et al., "The NPAS3 gene—emerging evidence for a role in psychiatric illness", 2006, pp. 439-448, XP-009108604, Annals of Medicine, vol. 38, No. 6, ISSN: 0785-3890.
Ehret et al., "Iloperidone: A novel atypical antipsychotic for the treatment of schizophrenia", 2008, pp. 190-196 + 203, XP-009108739, Formulary, vol. 43, No. 6, ISSN: 1082-801X.
European Patent Office, Office Action for Application Serial No. 08830514.9 dated Aug. 17, 2010, 7 pages.
European Patent Office, Office Action for Application Serial No. 08830514.9 dated Apr. 16, 2011, 3 pages.
Patent Cooperation Treaty, International Search Report for Patent Cooperation Treaty International Application No. PCT/US2008/064027, filed May 17, 2008, issued Nov. 25, 2008 by European Patent Office as International Search Authority.
Albers, L.J. et al., "Iloperidione: a new benzisoxazole atypical antipsychotic drug. Is it novel enough to impact the crowded atypical antipsychotic market?" Expert Opinion on Investigational Drugs, 2008 Informa Healthcare UK Ltd., vol. 17 No. 1, Jan. 2008, pp. 61-75.
Pickard, B.S. et al., "Disruption of a Brain Transcription Factor, NPAS3, Is Associated With Schizophrenia and Learning Disability," American Journal of Medical Genetics, vol. 136B No. 1, Jul. 2005, pp. 26-32.
Kamnasaran, D. et al., "Disruption of the neuronal PAS3 gene in a family affected with schizophrenia," Journal of Medical Genetics, vol. 40 No. 5, May 2003, pp. 325-332.
Mutlib, A.E. et al., "Application of Liquid Chromatography/Mass Spectrometry in Accelerating the Identification of Human Liver Cytochrome P450 Isoforms Involved in the Metabolism of Iloperidone," Journal of Pharmacology and Experimental Therapeutics, vol. 286 No. 3, Sep. 1998, pp. 1285-1293.
Subramanian, S. et al., "Receptor profile of P88-8991 and P95-12113, metabolites of the novel antipsychotic Ioperidone," Progress in Neuro-Psychopharmacology & Biological Psychiatry, vol. 26 No. 3, Jan. 1, 2002, pp. 553-560.
Hirschhorn et al., "A Comprehensive Review of Genetic Association Studies," Apr. 2002, pp. 45-61, Genetics in Medicine, vol. 4, No. 2.
Ioannidis et al., "Replication Validity of Genetic Association Studies," Nov. 2001, pp. 306-309, Nature Genetics, vol. 29.

(Continued)

*Primary Examiner* — Jehanne Sitton
(74) *Attorney, Agent, or Firm* — Hoffman Warnick LLC (57) ABSTRACT

The present invention relates to the prediction of antipsychotic treatment efficacy based on a patient's genotype at one or more single nucleotide polymorphism (SNP) loci and to the treatment of a patient based on such prediction.

12 Claims, 5 Drawing Sheets

(56) References Cited

OTHER PUBLICATIONS

Lavedan et al., "Association of the NPAS3 Gene and Five Other Loci with Resonse to the Antipsychotic Iloperidone Identified in a Whole Genome Association Study," 2009, pp. 804-819, Molecular Psychiatry, vol. 14.

Tacher et al., "Olfactory Receptor Sequence Polymorphism Within and Between Breeds of Dogs," Oct. 2005, pp. 812-816, Journal of Heredity, vol. 96, No. 7.

Goldberg, Office Action Communication for U.S. Appl. No. 12/600,036 dated Feb. 28, 2012, 23 pages.

Goldberg, Office Action Communication for U.S. Appl. No. 12/600,036 dated Jun. 14, 2012, 9 pages.

Goldberg, Office Action Communication for U.S. Appl. No. 12/600,036 dated Nov. 5, 2012, 12 pages.

Wei et al., "Association analysis of serotonin receptor 7 gene (HTR7) and risperidone response in Chinese schizophrenia patient," 2009, ages 547-551, Progress in Neuro-Psychopharmacology & Biological Psychiatry, vol. 33.

Hegele, "SNP Judgments and Freedom of Association," 2002, pp. 1058-1061, Arteriosclerosis, Thrombosis, and Vascular Biology, Journal of the American Heart Association, vol. 22.

Lucentini, "Gene Association Studies Typically Wrong," Dec. 2004, p. 20, The Scientist, vol. 24.

Juppner, "Functional Properties of the PTH/PTHrP Receptor," 1995, pp. 39S-42S, Bone, vol. 17, No. 2.

Sitton, Examiner Search Strategy and Results, ss24557736 (dbSNP, rs4528226; 2004) from U.S. Appl. No. 12/675,598 dated Dec. 31, 2012, 1 page.

Sitton, Office Action Communication for U.S. Appl. No. 12/675,598 dated Dec. 31, 2012, 25 pages.

Goldberg, Office Action Communication for U.S. Appl. No. 12/600,036 dated Sep. 19, 2013, 13 pages.

Office Action Communication for U.S. Appl. No. 12/600,036 dated Feb. 5, 2014, 12 pages.

Notice of Allowance and Fee(s) Due for U.S. Appl. No. 12/600,036, dated Apr. 15, 2015, 13 pages.

Office Action Communication for U.S. Appl. No. 12/600,036 dated Dec. 24, 2014, 12 pages.

Sitton, Final Office Action for U.S. Appl. No. 12/675,598 dated Aug. 7, 2013, 12 pages.

Sitton, Notice of Allowance and Fee(s) Due for U.S. Appl. No. 12/675,598 dated Dec. 31, 2015, 17 pages.

ANTIPSYCHOTIC TREATMENT BASED ON SNP GENOTYPE

CROSS-REFERENCE TO RELATED APPLICATIONS

This application claims the benefit of co-pending U.S. patent application Ser. No. 12/675,598, filed 26 Feb. 2010, which is the US national phase of PCT Patent Application No. PCT/US08/75845, filed 10 Sep. 2008, which claims priority to U.S. Provisional Patent Application No. 60/971,227, filed 10 Sep. 2007 and 61/018,548, filed 2 Jan. 2008, each of which is hereby incorporated herein.

SEQUENCE LISTING

The sequence listing contained in the electronic file titled "VAND-0056-US-CON_Seq_IDs_PatentIn.txt," created 30 Mar. 2016, comprising 3 KB, is hereby incorporated herein.

BACKGROUND OF THE INVENTION

Schizophrenia is a psychotic disorder affecting approximately 1% of the population. It is characterized by the presence of positive symptoms (unusual thoughts or perceptions, including hallucinations and delusions), negative symptoms (social withdrawal, lack of pleasure in everyday life), and impaired cognitive functions (verbal memory, information processing). Such symptoms may be indicative of other disorders, such as, for example, bipolar disorder.

A number of drugs have been approved to treat schizophrenia. However, patient response to treatment remains highly variable, and the discontinuation rate with antipsychotic treatment is high. No single antipsychotic agent offers optimal effect for every patient with schizophrenia. Few data are available to guide clinicians and patients in the selection of the most appropriate medication and in the improvement of treatment specificity for an individual patient. Pharmacogenomics provides the opportunity to discover genetic markers predictive of response. Knowing how a patient with schizophrenia might respond to a particular therapy based on his or her genetic makeup may enable clinicians to select the most optimal drug and dosage with less trial and error.

SUMMARY OF THE INVENTION

The present invention relates to the treatment of an individual with an antipsychotic based on the individual's genotype at one or more single nucleotide polymorphism (SNP) loci associated with antipsychotic response, as well as the prediction of how well an individual will respond to an antipsychotic based on the individual's genotype at one or more such SNP loci. More particularly, the invention relates to the treatment of an individual an atypical antipsychotic and/or the prediction of the efficacy of such treatment based on the individual's genotype at one or more SNP loci selected from a group consisting of: rs11851892, rs9643483, rs875326, rs2513265, rs7837682, and rs4528226. Atypical antipsychotics include, for example, iloperidone, clozapine, risperidone, olanzapine, quetiapine, siprasidone, aripiprazole, paliperidone, asenapine, sertindole, zotepine, amisulpride, bifeprunox, melperone, pharmaceutically-acceptable salts thereof, metabolites thereof, and pharmaceutically-acceptable salts of metabolites thereof.

One aspect of the invention provides a method of predicting the efficacy of using iloperidone, an iloperidone metabolite, or a pharmaceutically-acceptable salt of iloperidone or an iloperidone metabolite in the treatment of at least one psychotic symptom in an individual, the method comprising: determining the individual's genotype at at least one single nucleotide polymorphism (SNP) locus selected from a group consisting of: rs11851892, rs9643483, rs875326, rs2513265, rs7837682, and rs4528226; and in the case that the individual's genotype at the at least one SNP locus is associated with greater iloperidone efficacy, predicting that treating the individual with iloperidone will be efficacious.

Another aspect of the invention provides a method of determining the responsiveness of a human with a psychotic disorder or bipolar disorder to treatment with an atypical antipsychotic, the method comprising: determining the individual's genotype at at least one single nucleotide polymorphism (SNP) locus selected from a group consisting of: rs11851892, rs9643483, rs875326, rs2513265, rs7837682, and rs4528226; and in the case that the individual's genotype at the at least one SNP locus is associated with greater iloperidone efficacy, predicting that treating the individual with iloperidone will be efficacious.

Yet another aspect of the invention provides a method of treating a patient for one or more symptoms of a psychotic disorder, schizophrenia, or bipolar disorder, the method comprising: determining the patient's genotype in both copies of at least one single nucleotide polymorphism (SNP) locus selected from a group consisting of: rs11851892, rs9643483, rs875326, rs2513265, rs7837682, and rs4528226; and in the case that the patient has a genotype that is associated with iloperidone efficacy at at least one of the SNP loci, administering to the patient an effective amount of iloperidone, an iloperidone metabolite, or a pharmaceutically-acceptable salt of iloperidone or an iloperidone metabolite.

Another aspect of the invention provides iloperidone, an active metabolite of iloperidone, or a salt of iloperidone or of an active metabolite of iloperidone for use in the treatment of patients suffering from one or more symptoms of a psychotic disorder, schizophrenia, or bipolar disorder in a patient that has a genotype that is associated with iloperidone efficacy at at least one of the SNP loci selected from a group consisting of: rs11851892, rs9643483, rs875326, rs2513265, rs7837682, and rs4528226.

Still another aspect of the invention provides a kit for use in determining treatment strategy for a patient with a psychotic disorder, schizophrenia, or bipolar disorder comprising: (a) a polynucleotide able to recognize and bind to some portion of the DNA sequences that comprise at least one of the genetic loci identified in claim 1; (b) a container suitable for containing the said polynucleotide and a sample of chromosomal DNA from the said individual wherein the polynucleotide can contact the chromosomal DNA, and (c) means to detect the combination of the said polynucleotide with the chromosomal DNA sequence and thereby to ascertain what the genotype of the individual is at the one or more of the six loci.

Another aspect of the invention provides a method of marketing an atypical antipsychotic, the method comprising: informing a prescriber, a patient, or both, that the atypical antipsychotic is more effective in individuals having a genotype associated with increased iloperidone efficacy.

Yet another aspect of the invention provides a method of selecting individuals for a clinical trial, the method comprising: determining an individual's genotype at at least one single nucleotide polymorphism (SNP) locus selected from a group consisting of: rs11851892, rs9643483, rs875326, rs2513265, rs7837682, and rs4528226; and including or excluding the individual from a clinical trial based on the individual's genotype at one or more of the SNP loci.

DETAILED DESCRIPTION OF THE INVENTION

Iloperidone (1-[4-[3-[4-(6-flouro-1,2-benzisoxazol-3-yl)-1-piperidinyl]propoxy]-3-methoxyphenyl] ethanone) is disclosed in U.S. Pat. RE39198, which is incorporated herein by reference. Active metabolites of Iloperidone are useful in the present invention. See, e.g., WO03020707, which is incorporated herein by reference. Iloperidone metabolites include: 4-[3-[4-(6-Fluoro-1,2-benzisoxazol-3-yl)-1-piperidinyl]propoxy]-3-methoxy-a$\alpha$-methylbenzene methanol, 1-[4-[3-[4-(6-Fluoro-1,2-benzisoxazol-3-yl)-1-piperidinyl]propoxy]-3-hydroxyphenyl]ethanone, 1-[4-[3-[4-(6-Fluoro-1,2-benzisoxazol-3-yl)-1-piperidinyl]propoxy]-3-methoxyphenyl]-2-hydroxyethanone, 4-[3-[4-(6-Fluoro-1,2-benzisoxazol-3-yl)-1-piperidinyl]propoxy]-3-hydroxy-a$\alpha$-methylbenzene methanol, 4-[3-[4-(6-Fluoro-1,2-benzisoxazol-3-yl)-1-piperidinyl]propoxy]-2-hydroxy-5-methoxy-a$\alpha$-methylbenzene methanol, 1-[4-[3-[4-(6-Fluoro-1,2-benzisoxazol-3-yl)-1-piperidinyl]propoxy]-2-hydroxy-5-methoxyphenyl]ethanone, and 1-[4-[3-[4-(6-Fluoro-1,2-benzisoxazol-3-yl)-1-piperidinyl]propoxy]-2,5-dihydroxyphenyl]ethanone. See, US RE39198, WO93/09276 and WO95/11680, which are incorporated herein by reference.

An effective amount of iloperidone or an active metabolite thereof may be administered to a subject animal (typically a human but other animals, e.g., farm animals, pets and racing animals, can also be treated) by a number of routes. An effective amount is an amount that during the course of therapy will have a preventive or ameliorative effect on a psychotic disorder, such as schizophrenia, or a symptom thereof, or of bipolar disorder. An effective amount, quantitatively, may vary, depending upon, for example, the patient, the severity of the disorder or symptom being treated, and the route of administration.

It will be understood that the dosing protocol including the amount of iloperidone or an active metabolite thereof actually administered will be determined by a physician in the light of the relevant circumstances including, for example, the condition to be treated, the chosen route of administration, the age, weight, and response of the individual patient, and the severity of the patient's symptoms. Patients should of course be monitored for possible adverse events.

For therapeutic or prophylactic use, iloperidone or an active metabolite thereof will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of iloperidone or an active metabolite thereof. See, for example, Remington's Pharmaceutical Sciences, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the required pharmaceutical carrier.

Iloperidone and its active metabolites can also be formulated in a controlled release form, e.g., delayed, sustained, or pulsatile release.

Various formulations and methods of administering iloperidone and/or its derivatives have been described. For example, PCT Publication No. WO 2004/006886 A2 describes an injectable depot formulation comprising iloperidone crystals, microencapsulated depot formulations of iloperidone and a polyglycolide polylactide glucose star polymer are described in U.S. 20030091645, and methods for the administration of iloperidone directed toward, inter alia, eliminating or minimizing the prolongation of a corrected electrocardiographic QT (QTc) interval associated with increased concentrations of iloperidone or iloperidone derivatives are described in PCT Publication No. WO 2006/039663 A2, all of which are incorporated herein by reference.

Several single nucleotide polymorphisms (SNPs) were found to be associated with improved response to iloperidone following a whole genome association study (WGAS) performed in a phase 3 clinical trial of iloperidone. The clinical trial evaluated the efficacy of iloperidone in treating patients with diagnosed schizophrenia.

The SNPs identified as predictive of a patient's response to iloperidone treatment were found within the neuronal PAS domain protein 3 gene (NPAS3), the XK, Kell blood group complex subunit-related family, member 4 gene (XKR4), the tenascin-R gene (TNR), the glutamate receptor, ionotropic, AMPA4 gene (GRIA4), the glial cell line-derived neurotrophic factor receptor-alpha2 gene (GFRA2), and the NUDT9P1 pseudogene located in the chromosomal region of the serotonin receptor 7 gene (HTR7).

Patients 18 to 65 years of age with diagnoses of schizophrenia according to the *Diagnostic and Statistical Manual of Mental Disorders, 4th Edition* were eligible to participate in a randomized, double-blind, placebo- and ziprasidone-controlled, 28-day study of the efficacy and safety of iloperidone. Patients were randomly assigned to iloperidone 12 mg twice a day, ziprasidone 80 mg twice a day (active control), or placebo. The primary efficacy variable was change from baseline to the last scheduled observation in Positive and Negative Syndrome Scale total score (PANSS-T) using the data from the short-term, double-blind phase. A secondary objective was to identify genetic markers predictive of response to iloperidone.

Blood samples were collected, and DNA was extracted from 432 of 457 patients who consented to the optional WGAS, including 218 patients administered iloperidone and 102 administered placebo.

To independently discover and confirm biomarkers of iloperidone efficacy, patients administered iloperidone were randomly separated and genotyped for the WGAS into two groups (Group 1 (discovery phase) and Group 2 (confirmatory phase)) of equal size. PROC SURVEYSELECT (SAS Institute, Cary, N.C.) was used to stratify the groups to have approximately equal numbers of patients of each race and each sex.

In Group 1, each SNP was tested for potential association between genotype and change in PANSS-T for patients in the low 30% and the high 30% extremes of the distribution of Day 28 last-observation-carried-forward (LOCF) data. Analysis was performed using a truncated nonparametric measure analysis of variance (ANOVA), based on the Kruskal-Wallis test, with genotypes as the grouping variables. Based on a significant omnibus test and ad hoc contrasts, the results that produced the most parsimonious genetic model (e.g., homozygous for one allele vs. all other genotypes (e.g., AA vs. AB and BB), heterozygous vs. homozygous genotypes (AB vs. AA and BB)) dictated the genetic model that was tested in the confirmatory phase. For ease of global description, given that each SNP might have a different parsimonious model, the genotypes of all SNPs associated with positive iloperidone response were referred to as genotype class C1, and the remaining genotypes for that SNP were referred to as genotype class C2. If no parsimonious genetic model was obtained for a SNP, it was not tested further. Only the subset of 100 SNPs with the lowest P values for the contrasts that defined C1 and C2 was tested in the confirmatory phase.

Two separate methods were applied. LOCF data for PANSS-T at Day 28 were used in a one-way ANOVA of each SNP, testing each genotype class against the class of the other two genotypes combined. Results from the ANOVA dictated the parsimonious genetic model to be used for additional testing. Mixed Model Repeated Measures (MMRM) analysis was subsequently conducted using the parsimonious genetic model of each SNP in the MMRM model, as used for the analysis of the clinical trial results. In the MMRM analysis, only the best genetic model of each SNP, as determined in the ANOVA LOCF data analysis, was used.

In the confirmatory step of the two-phase approach, Bonferroni corrections of $\alpha=0.05/100$ were applied. False discovery rate (FDR) corrections were also calculated using the Benjamini and Hochberg (BH) procedure. Within each of the two single-phase analyses, the BH procedure was used. SNPs with the lowest P values were analyzed without any specific threshold. FDR corrections were obtained from PROC MULTTEST (SAS Institute), which produces BH adjustments to original analytical P values.

DNA samples were genotyped for more than 500,000 SNPs using a microarray set (GeneChip Human Mapping 500K Array Set; Affymetrix, Santa Clara, Calif.) according to the manufacturer's instructions. The set was composed of two arrays, each capable of genotyping on average 250,000 SNPs (~262,000 for Nsp arrays and 238,000 for Sty arrays).

DNA samples were also genotyped for additional polymorphisms previously studied for association with schizophrenia or antipsychotic treatment but not represented on the microarray set (GeneChip Human Mapping 500K Array Set; Affymetrix). These SNPs were genotyped using either polymerase chain reaction (PCR) followed by restriction fragment length polymorphism (RFLP) detection or by allele-specific primer (ASP) PCR (see Table 1).

Each PCR reaction contained 60 ng DNA, 1x PCR reaction buffer with $MgSO_4$ (0.5 mM), DNA polymerase (AmpliTaq; Applied Biosystems, Foster City, Calif.), 5 pmol dNTP mix (Promega, Madison, Wis.), and 10 pmol of each specific primer in a total volume of 25 µL. For the ASP assays, HotStarTaq® polymerase (Qiagen, Valencia, Calif.) was used, and two PCR reactions were performed for each sample, one for each allele. PCR conditions were as follows: 95° C. initial denaturation for 10 minutes, then 35 cycles of 30-second denaturation at 95° C., 30-second annealing (temperature specific to SNP), 1-minute extension at 72° C., and finally 10-minute extension at 72° C. PCR products were digested with the appropriate restriction enzyme and separated on a 4% agarose gel against standard DNA ladders to determine fragment sizes.

To ensure the integrity of the data collected from DNA arrays, the following quality control steps were taken:

Algorithms

Each microarray (GeneChip® Human 500K Array Set; Affymetrix) was analyzed with the dynamic model-based genotyping algorithm and with the latest Bayesian robust linear model with Mahalanobis (BRLMM) distance classifier with a confidence threshold of 0.5. Under these conditions, missing genotypes were assumed missing at random, and no imputation was made for any genetic data. The BRLMM Analysis Tool 2.0 and the SNP Signal Tool 1.0.0.12. (Affymetrix) were used to analyze and visualize the distribution and separation of genotype calls of individual SNPs.

Call Rate

Call rate was defined for a single array as the percentage of SNPs that were called AA, AB, or BB by the BRLMM algorithm. Only arrays with call rate were retained for further analysis.

Concordance Between Arrays

Of the more than 500,000 SNPs genotyped, 50 were common to both the Sty and the Nsp arrays. Only arrays with >90% concordance for these SNPs were used in further analysis.

Uniqueness of Samples

The ~250,000 SNP data obtained per sample on each array (Sty or Nsp) were compared with the genotypes of all other samples to identify potential duplicate samples. IF >90% of the genotypes were identical between two arrays, DNA was retested to confirm genotypes and, if necessary, to eliminate duplicate samples.

Lack of DNA Contamination

Lack of DNA contamination of a sample by another sample was assessed for each array by determining the overall percentage of SNPs with heterozygote calls, as calculated by the dynamic model-based algorithm. Genotype calls from arrays with <30% heterozygote calls were considered to have come from a pure DNA sample. Only arrays with <30% heterozygote calls were used for further analysis.

Sex Determination

For each DNA sample, sex was blindly determined by the BRLMM algorithm based on the percentage of heterozygosity of the SNPs on the X chromosome. The result was compared with the expected sex. In case of divergent data, a PCR-based assay for the amelogenin gene (AMELX) was performed on the original sample and on a new DNA aliquot. A new genotyping experiment was performed with the Sty and Nsp arrays. Samples with incompatible results were excluded from the WGAS.

Allele Frequency

Focus was given to the most common polymorphisms by selecting SNPs with minor allele frequencies greater than or equal to 10%.

SNP Selection

A reference DNA (Human Genomic DNA 103 Control; Affymetrix) with available genotypes for SNPs on the microarray set (GeneChip Human 500K Array; Affymetrix) was systematically tested in parallel with the patient samples. Eight DNA 103 replicates for the Sty and Nsp arrays were obtained and analyzed. Individual SNP assays were considered to make accurate and reproducible calls (concordant calls) when the calls (AA, AB, BB) were identical across the eight replicates and identical to the reference calls provided by Affymetrix. Only SNPs with 100% concordance for DNA 103 were retained for the WGAS. Five SNPs that cross-hybridized with the Y chromosome and all SNPs on the X chromosome were not used. The total number of SNPs analyzed in this WGAS was 334,563.

DNA Sequencing

For each SNP of interest, a minimum of 15 DNA samples were sequenced that included at least five samples for each homozygote and heterozygote genotype. The following primers were used for PCR amplification (as described in "Genotyping methods," with 55° C. annealing), before sequencing:

5'-CAT GCA GCT ATG TTT GGG AG-3' (forward; SEQ. ID No. 1) and 5'-GCC AAA ATA ATG TGT AGC AAT C-3' (reverse; SEQ. ID No. 2) for rs11851892;

5'-GAT TGG CTT TGG GTT TGC CTT G-3' (forward; SEQ. ID No. 3) and 5'-GAC CCC ATC TTT AGC GGA AC-3' (reverse; SEQ. ID No. 4) for rs9643483;

5'-GAA GGG TCT ACC TCG ATT CC-3' (forward; SEQ. ID No. 5) and 5'-GAT CAG CTT ATT CAA CCC TC-3' (reverse; SEQ. ID No. 6) for rs875326;

5'-CTA AAG GCG AAA CAT GTG TAT G-3' (forward; SEQ. ID No. 7) and 5'-CAT AGC AGC TGA CCA ACA TTC C-3' (reverse; SEQ. ID No. 8) for rs2513265;

5'-CAA TCT GCT TTC ACC TCA ACC C-3' (forward; SEQ. ID No. 9) and 5'-CTG CCA CCC TAC TCA ACA CC-3' (reverse; SEQ. ID No. 10) for rs7837682; and 5'-GAG CAG ATA AAT TTG CCT GG-3' (forward; SEQ. ID No. 11) and 5'-GTT GAA CCC AAA GAC ACC CCT G-3' (reverse; SEQ. ID No. 12) for rs4528226.

Sequencing was performed with a reagent kit (GeneAmp® PCR Reagent Kit with AmpliTaq® DNA Polymerase; Applied Biosystems) according to the manufacturer's instructions for a 25-µL reaction. Nucleotide sequences were determined using an automated capillary DNA sequencer (Avant 3100; Applied Biosystems) and a cycle sequencing kit (BigDye® Terminator version 3.1 Cycle Sequencing Kit; Applied Biosystems) according to the manufacturer's instructions.

Results

The effectiveness of iloperidone for the treatment of schizophrenia was assessed using PANSS. Genetic association with the change in the PANSS-T between baseline and Day 28 was tested for 334,563 SNPs. In an association study with such a large number of SNPs, the selection of the best candidates is based on extreme P values. These may be more sensitive than usual to the particulars of the statistical method used. Thus, to select the most likely markers of the efficacy of iloperidone, several analytical methods were used and focus given to those SNPs with persistently low P values across the different methods.

Three analyses were performed. Analysis 1 was a two-phase approach in which DNA samples were separated into two groups. The first group consisted of 50% of the samples for a discovery phase in which only the top 30% and the bottom 30% of the change in PANSS-T (LOCF data) were used, and the second was a hold-out group consisting of the other 50% for a confirmatory phase. Only the 100 SNPs with the lowest P values in the discovery phase were subsequently tested.

Analysis 2 was an ANOVA of LOCF data for all iloperidone-treated patients in a single-phase approach.

Analysis 3 was an MMRM analysis of all patients using the most parsimonious genetic model of each SNP. The two single-phase approaches (Analyses 2 and 3) provided more power to detect significant associations by taking advantage of all available samples.

Figure 1A:
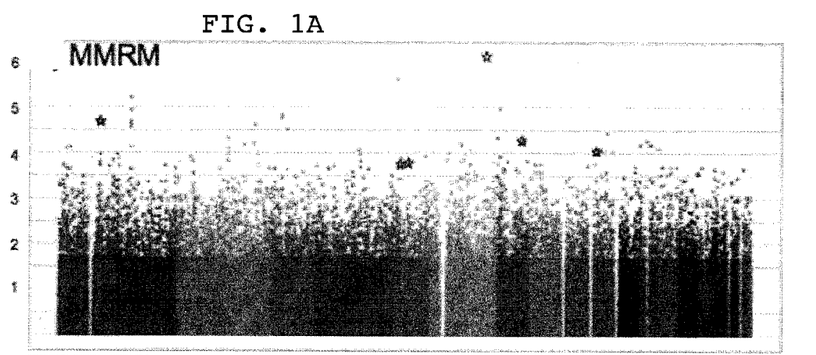
FIGS. 1A and 1B show the results, respectively, of mixed model repeated measures (MMRM) analysis and last-observation-carried-forward (LOCF) analysis, of iloperidone response in the treatment of patients with schizophrenia per chromosome. Each point shows the P value (logarithmic scale on vertical axis) and the genomic location (horizontal axis) of one SNP for the association of change in PANSS-T using the most parsimonious genetic model of that SNP. Arrows point to selected SNPs described in the specification.
Figure 1B:
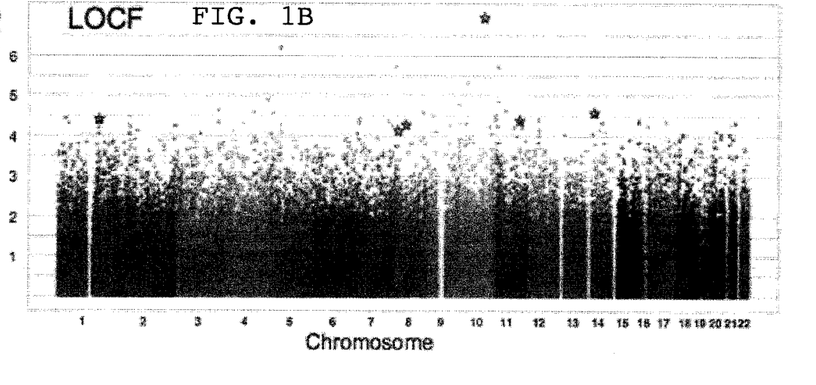

Overall whole genome association results from the LOCF and MMRM single-phase approaches are shown in FIG. 1. Forty-five of the 100 SNPs with the lowest P values were common between these two analyses. Six of these SNPs were also among the top 100 SNPs of the two-phase analysis. More detail regarding these six SNPs (rs11851892, rs9643483, rs875326, rs2513265, rs7837682, rs4528226) and their association with iloperidone response are shown in Table 2. Data from the different treatment groups were used in the MMRM statistical model, which allowed a comparison of genotype effect between iloperidone treatment and placebo. Except when otherwise specified, results discussed herein refer to PANSS-T data and to P values generated from the MMRM analysis.

NPAS3 and Iloperidone Response

Figure 2A:
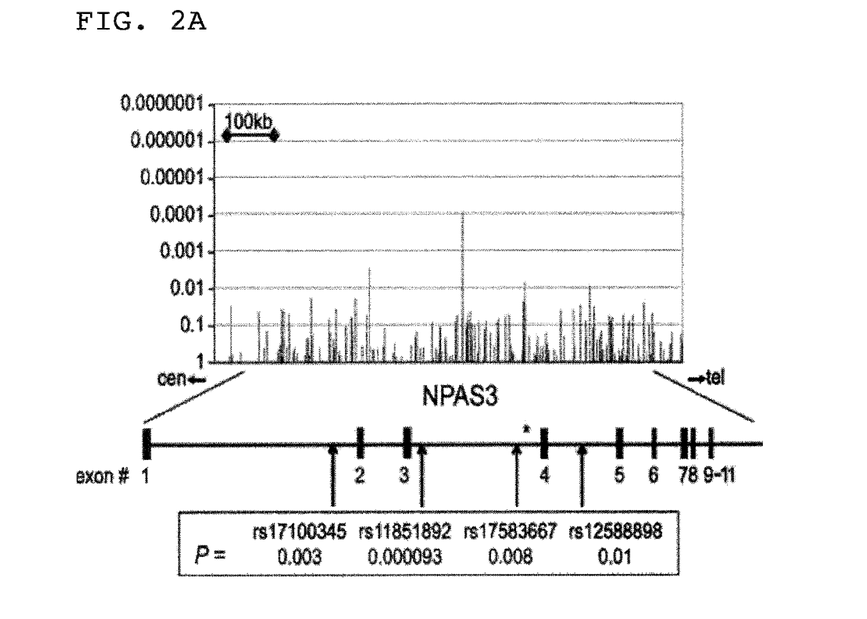
FIGS. 2A-2F show, respectively, the genetic association between change in PANSS-T and SNPs in the NPAS3, XKR4, TNR, GRIA4, GFRA2, and NUDT9P1 gene regions. P values (vertical axis) from the MMRM analysis are shown for the genomic regions containing NPAS3 (FIG. 2A), XKR4 (FIG. 2B), TNR (FIG. 2C), GRIA4 (FIG. 2D), GFRA2 (FIG. 2E), and NUDT9P1 (FIG. 2F) in order of the SNPs' physical locations (horizontal axis). The direction of the maps relative to the centromere (cen) and to the telomere (tel) is indicated by horizontal arrows. SNPs with P≤0.01 are boxed. The approximate location in NPAS3 of the breakpoint described by Kamnasaran et al. in a family with schizophrenia is indicated by an asterisk (*).

SNP rs11851892 is located on chromosome 14q12-q13 within intron 3 of the NPAS3 gene, which codes for the neuronal PAS domain protein 3. Three other SNPs within this gene were also significant at the P<0.01 level (see FIG. 2a).

The non-GG rs11851892 genotype, which had a frequency of 31%, was present in a group of iloperidone-treated patients who averaged >20-point improvement from baseline in PANSS-T (−20.12 [±3.69]), 68% greater than the mean response (−12.01 [±1.03]) of all iloperidone-treated patients (see Table 3). Patients who carried the non-GG genotype were approximately three times more likely to experience 20% improvement than patients who carried the GG genotype (odds ratio [OR]=2.74, P=0.0011; see Table 4).

The NPAS3 gene has previously been linked to schizophrenia. Kamnasaran et al. describe a mother and daughter with schizophrenia who were carriers of a chromosome translocation, t(9;14)(q34;q13). Two of the SNPs associated with change in PANSS-T in the WGAS (rs11851892, rs17583667) were localized within the same intron 3 of NPAS3 as the breakpoint observed in this family (see FIG. 2a).

XKR4 and Iloperidone Response

SNP rs9643483 is located in 8q12.1. Its GG genotype was present in approximately 22% of iloperidone-treated patients, who, on average, experienced smaller changes in PANSS-T than patients with different genotypes (−3.30 [±3.93] vs −15.02 [±4.34], respectively) and than patients who received placebo (Table 3). Patients who carried the non-GG genotype were approximately 3.5 times more likely to experience 20% improvement than patients who carried the GG genotype (odds ratio [OR]=3.42, P=0.0009; Table 4).

Figure 2B:
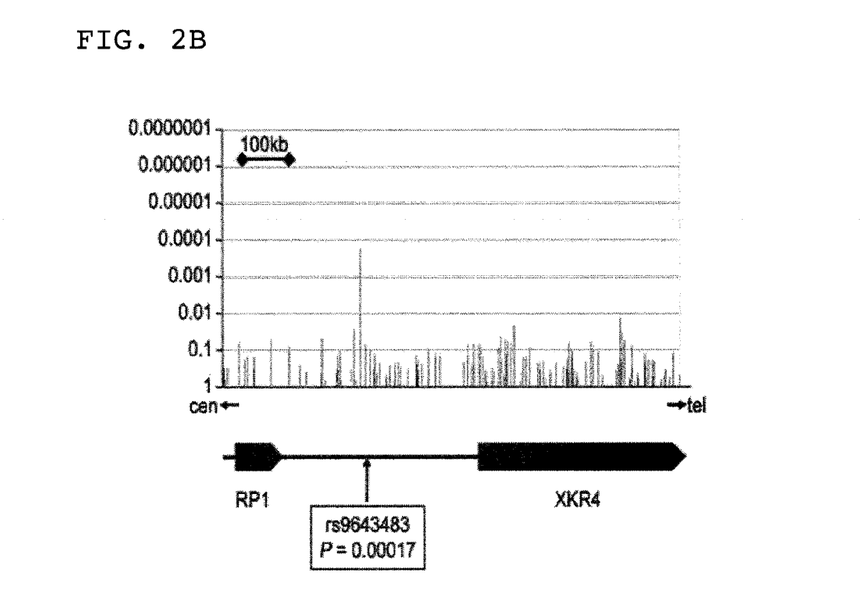

SNP rs9643483 lies between the XK-Kell blood group complex subunit-related family, member 4 (XKR4) gene (~220 kb away) and the retinitis pigmentosa 1 (RP1) gene (~250 kb away). No other SNPs in that region were significant at the P<0.01 level (FIG. 2b).

The XKR4 gene codes for a protein related to the XK protein. Kell and XK are two distinct red blood cell membrane proteins that form the Kell blood group complex (FIG. 2b). XK is a putative membrane transporter whose substrate is unknown, but absence of the protein is associated with McLeod syndrome. This rare, genetic, X-linked disease is characterized by red blood cell acanthocytosis and late-onset central nervous system (CNS) and neuromuscular abnormalities. CNS manifestations include cognitive impairment, psychopathology, seizures, and choreatic movements. One report has mentioned schizophrenia as a manifestation of McLeod syndrome. Mutations in the RP1 gene have been reported to cause dominant retinitis pigmentosa. The specific role of the protein encoded by this gene is still unknown, but it is thought to be important in photoreceptor biology. The association of retinitis pigmentosa with features of psychosis has been reported in patients with Usher syndrome, but it is not well understood. No reports have been published of an association between XKR4 or RP1 and schizophrenia or response to antipsychotic treatment.

TNR and Iloperidone Response

Figure 2C:
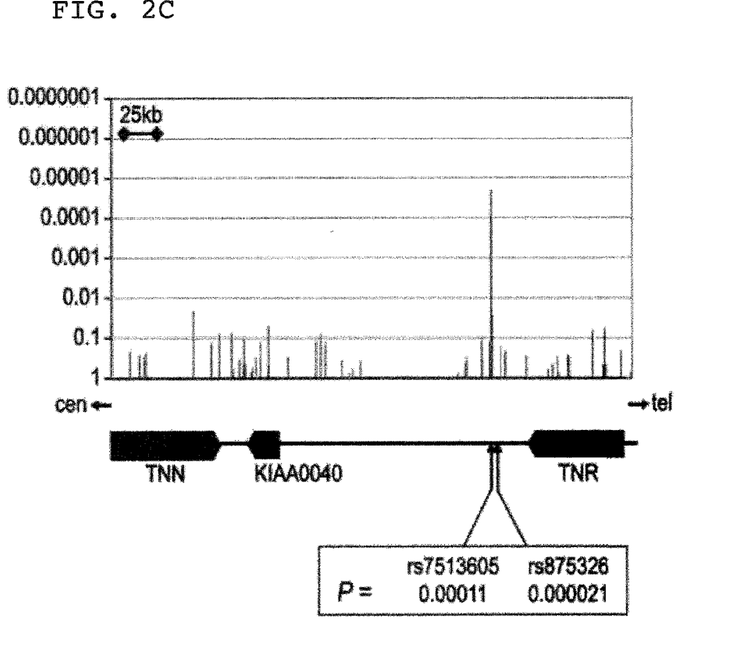

Another SNP of interest is rs875326 on 1q25.1, located between the TNR (~2.5 kb away) and TNN genes (~170 kb away), which encode the tenascin-R and -N proteins, respectively. The genomic region between TNR and TNN also contains the KIAA0040 locus of still unknown function (FIG. 2c). The rs875326 homozygote genotypes were associated with the highest response to iloperidone treatment, with a mean change in PANSS-T of −16.39 (±4.35) compared with a mean change of −6.21 (±4.51; P=0.000021) for patients with the heterozygote genotype (Table 3). More than 63% of iloperidone-treated patients homozygote for rs875326 were approximately 3.5 times more likely to experience 20% improvement than those who carried the AG genotype (OR=3.57, P<0.0001; Table 4).

Tenascin-R is an extracellular matrix protein expressed primarily in the CNS and localized around motor neurons and on motor axons in the spinal cord, cerebellum, hippocampus, and olfactory bulb. It is a member of the tenascin gene family, which includes at least three other genes in humans—TNN on 1q, TNC on 9q33, and TNXB on 6p21.3. TNXB deficiency leads to a clinically distinct, autosomal recessive form of Ehlers-Danlos syndrome, a severe connective tissue disorder. Two SNPs in the TNXB gene are associated with schizophrenia in a British population. To date, no direct evidence has implicated TNR or TNN in schizophrenia or in the response to antipsychotic treatment.

GRIA4 and Iloperidone Response

Figure 2D:
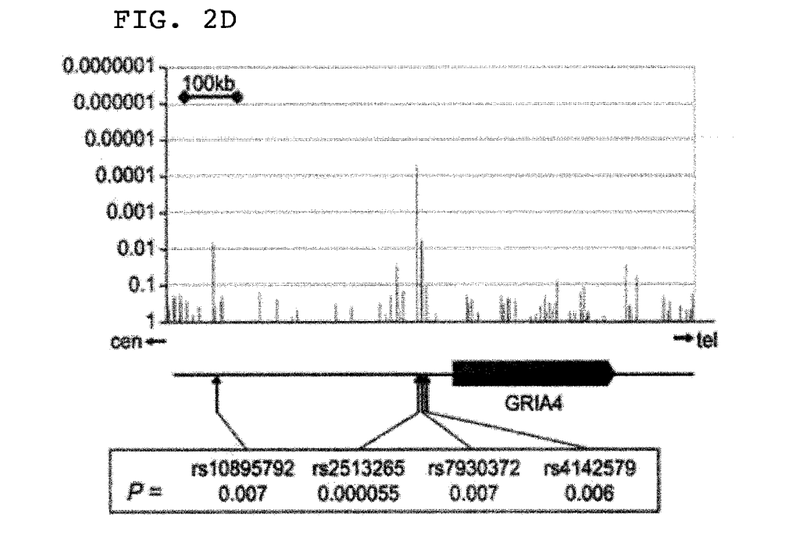

SNP rs2513265 is located on chromosome 11q22, approximately 58 kb from the 5' end of the glutamate receptor, ionotropic, AMPA 4 (GRIA4) gene (FIG. 2d). The rs2513265 TT genotype was present in approximately 23% of iloperidone-treated patients who, on average, experienced PANSS-T changes lower than those of patients with a different genotype (−3.30 [±4.11] vs −15.22 [±4.26], respectively) and comparable to those of patients receiving placebo (Table 3). Patients who carried the non-TT genotype were approximately 2.5 times more likely to experience 20% improvement than patients who carried the TT genotype (odds ratio [OR]=2.43, P=0.011; Table 4). Two other SNPs, rs7930372 and rs4142579, located within approximately an 8-kb interval, were also significant at P<0.01 (FIG. 2d). Interestingly, some haplotypes of the GRIA4 gene have shown a positive association with schizophrenia in the Japanese population.

GFRA2 and Iloperidone Response

SNP rs7837682 is located in the 8p21 region, where the schizophrenia susceptibility locus referred to as SCZD6 has been mapped through a number of positive genetic association studies. The rs7837682 AA genotype was associated with the highest response to iloperidone treatment, with a mean change in PANSS-T of −15.95 (±4.23) compared with a mean change of −6.08 (±4.28; P=0.00018) for patients with a different genotype (Table 3). More than 58% of iloperidone-treated patients who were homozygote AA for rs7837682 were approximately three times more likely to experience 20% improvement than were patients who carried a different genotype (OR=2.95; P=0.0004, Table 4).

Figure 2E:
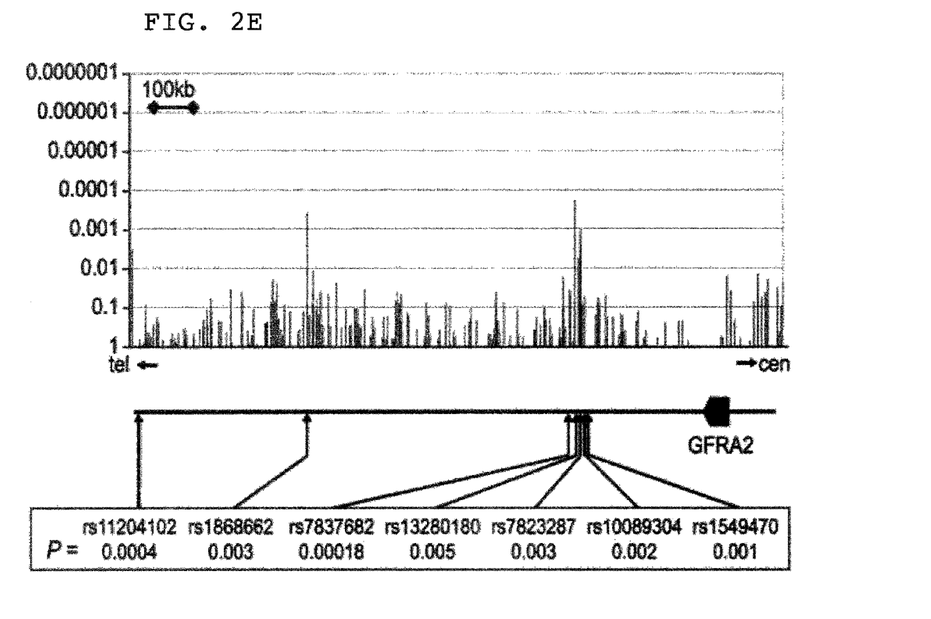

The closest known gene from rs7837682 is glial cell line-derived neurotrophic factor (GDNF) receptor-alpha2 (GFRA2), located approximately 360 kb away. Six other SNPs downstream of this gene were also significant at the P<0.01 level, including four SNPs within approximately 15 kb (FIG. 2e). GFRA2 codes for GDNF receptor-beta (GD-NFR-β). GDNF plays a key role in the control of neuron survival and differentiation. Results from a study in an Italian population suggest that a 3'UTR GDNF repeat polymorphism is associated with schizophrenia.

NUDT9P1 and Iloperidone Response

SNP s4528226 was the only SNP that showed a statistically significant association in the two-phase approach analysis at the P<0.05 level after correction for multiple testing using either the Bonferroni or the FDR method (Table 2). This SNP also showed the most significant statistical association when using all samples from the iloperidone-treated group, with either the LOCF or the MMRM method (Table 2). The rs4528226 GT genotype was associated with the highest response to iloperidone treatment, with a mean change in PANSS-T of −18.73 (±3.99) compared with a mean change of −6.61 (±4.29; P=0.00000078) for patients with a different genotype (Table 3). More than 47% of iloperidone-treated patients heterozygote for rs4528226 were three times more likely to experience a 20% improvement than homozygote patients (OR=3.00, P=0.0001; Table 4).

Figure 2F:
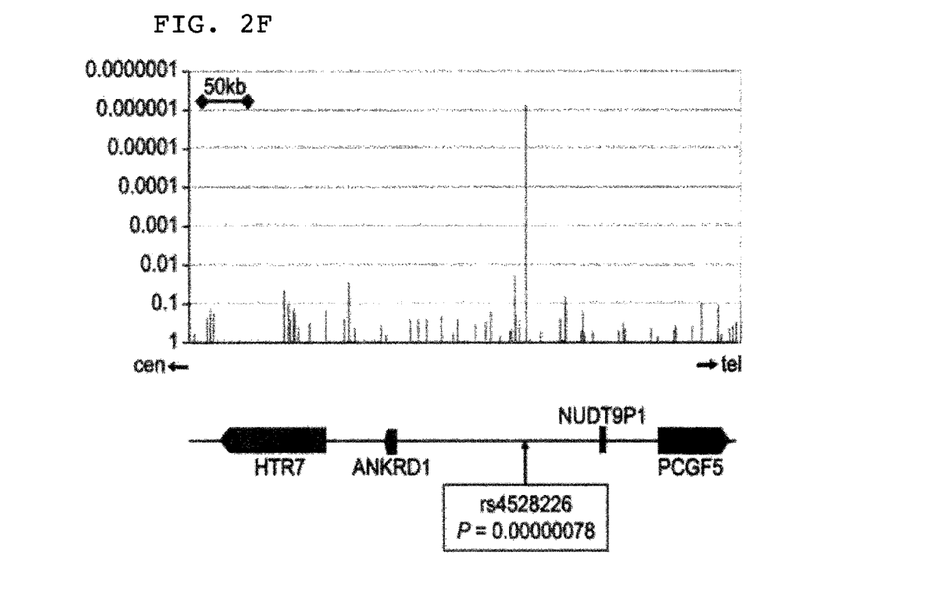
Figure 3A:
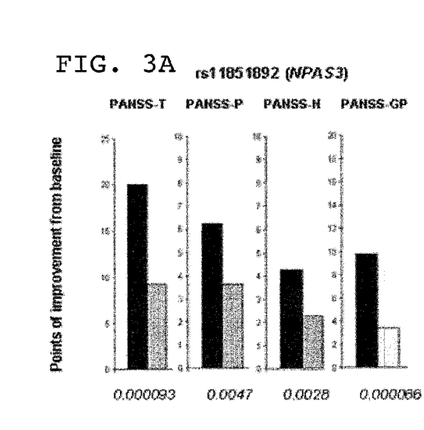
FIGS. 3A-3F show, respectively, the genotypes with the highest and lowest response to iloperidone in the SNPs identified in the NPAS3 (FIG. 3A), XKR4 (FIG. 3B), TNR (FIG. 3C), GRIA4 (FIG. 3D), GFRA2 (FIG. 3E), and NUDT9P1 (FIG. 3F) genes.
Figure 3B:
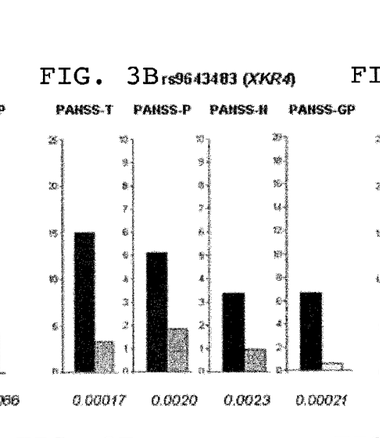
Figures 3C, 3F:
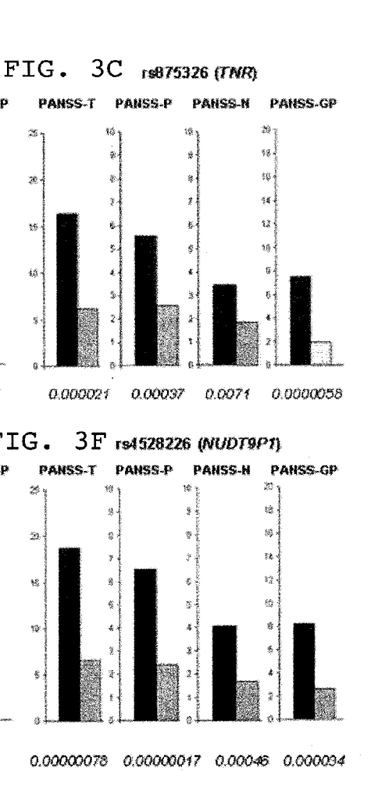
Figure 3D:
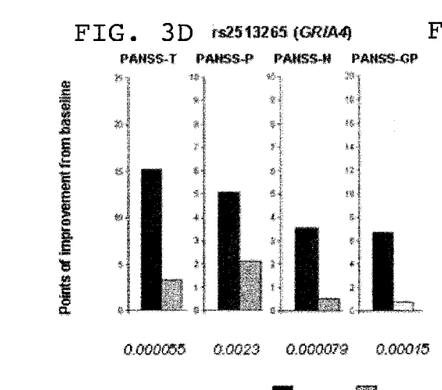
Figure 3E:
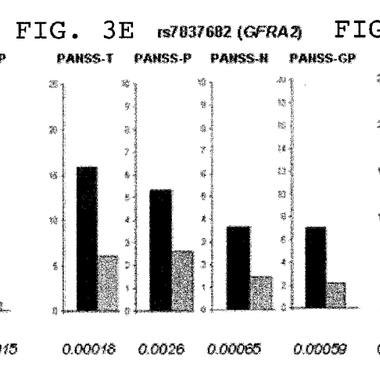

SNP rs4528226 is located on chromosome 10q23.31, close to the NUDT9P1 pseudogene, between the ankyrin repeat domain (ANKRD1) gene and the polycomb group ring finger 5 (PCGF5) gene, approximately 200 kb from the serotonin receptor 7 (HTR7) gene (FIG. 2f). No other SNPs in the same chromosomal region showed a statistically significant association at the P<0.01 level, including the closest flanking SNPs located 3.5 and 6.3 kb away. The HTR7 gene, which is considered a possible schizophrenia-susceptibility factor, has been associated with schizophrenia in a Japanese population. No link has been reported between schizophrenia or the response to antipsychotic treatment and NUDT9P1, ANKRD1, or PCGF5.

Analysis of Sex and Race

SNP allele frequencies can vary between races, and recombination rates depend on sex; therefore, ad hoc analyses of these potential confounding factors were conducted. For all SNPs reported herein, the association of a particular genotype with higher or lower response was consistent between men and women and across races, indicating that the significant associations observed were not attributable to bias resulting from the heterogeneity of the patient population studied.

Odds Ratio, Sensitivity, Specificity, and Predictive Values of Selected SNPs

To better appreciate the potential clinical value of the markers in predicting response to iloperidone, odds ratios (OR) and sensitivity, specificity, and predictive values of each selected marker were calculated (Table 4). SNP rs11851892 (NPAS3), which differentiated 31% of patients with superior iloperidone response, had the highest specificity (79%) and the strongest positive predictive value (65%). The two SNPs that differentiated a small group (<23%) of iloperidone-treated patients with lower changes in PANSS-T, rs9643483 (XKR4), and rs2513265 (GRIA4), had the highest sensitivity (88% and 85%, respectively). The other SNPs had intermediate values.

Validation of Genotype Calls

Genotype calls generated by the microarray set were also determined by sequencing on a random subset of DNA samples of iloperidone-treated patients. An accuracy rate of 100% was observed for rs11851892 (NPAS3), rs9643483 (XKR4), rs875326 (TNR), rs2513265 (GRIA4), and rs4528226 (NUDT9P1) and an accuracy rate of 95% was observed (35 of 37) for rs7837682 (GRFA2). The two erroneous calls detected for rs7837682 concerned changes of genotypes (AG vs GG) within the same genotype class (non-AA) that did not affect analyses of this SNP (AA vs non-AA).

SNP rs11851892, within the NPAS3 gene, identified a group of 31% of iloperidone-treated patients who experienced greater improvement in PANSS-T. Two independent linkage studies have suggested that a susceptibility locus for schizophrenia resides in chromosome 14q13. The NPAS3 gene, located on 14q13.1, has already been linked to schizophrenia in a family in which a mother and a daughter with the illness were carriers of a t(9;14)(q34;q13) translocation with a breakpoint in intron 3. Of the NPAS3 SNPs significantly associated with change in PANSS-T in the above study, two were in intron 3, including rs11851892, which had the most significant association for that region (P=0.000028 for ANOVA LOCF; P=0.000093 for MMRM). The NPAS3 protein belongs to a family of transcription factors that contain a basic helix-loop-helix region followed by a period/aryl hydrocarbon receptor/single-minded (PAS) domain. Kamnasaran et al. showed that the NPAS3 protein is expressed in multiple adult brain tissues, including the hippocampus, thalamus, and cortex. They proposed that haploinsufficiency of NPAS3 played a role in schizophrenia in the family with the intron 3 breakpoint. Additional evidence supporting the potential role of NPAS3 in schizophrenia comes from recent studies of mice. Pieper et al. showed that NPAS3-deficent mice manifest behavioral and neuroanatomic abnormalities reminiscent of schizophrenia. Erbel-Sieler et al. demonstrated that NPAS3-homozygous adult mice had marked reductions in reelin in the cortex, dentate gyrus, and amygdala. Reelin is an extracellular matrix protein thought to control cell-cell interactions critical for cell positioning and neuronal migration during brain development. In one genetics study, it has been suggested that reelin is associated with treatment-resistant schizophrenia, and it has been shown that levels of reelin and its mRNA are significantly reduced in several brain areas of patients with undifferentiated or paranoid schizophrenia. The results of the above study provide the first evidence of a possible link between NPAS3 and the efficacy of an antipsychotic treatment.

Of the other SNPs associated with change in PANSS-T in iloperidone-treated patients, several were of particular interest, including SNPs upstream of the GRIA4 gene. GRIA4 is a member of L-glutamate-gated ion channels, which mediate fast synaptic excitatory neurotransmission. This type of receptor is thought to modulate glutamatergic transmission in the brain by inhibiting glutamate release at the synapse. Although the specific AMPA4 glutamate receptor has not been extensively studied, an association between GRIA4 haplotypes and schizophrenia has been reported in a Japanese population. This finding was not seen in a Chinese population, and no studies of other populations have been reported. A potential role for glutamate in schizophrenia was first proposed based on the observation that the psychotomimetic agents phencyclidine (PCP) and ketamine induce psychotic symptoms and neurocognitive disturbances similar to those of schizophrenia by blocking neurotransmission at NMDA-type glutamate receptors. Since then, evidence of glutamate dysregulation in schizophrenia has been increasing.

Additionally, several SNPs associated with iloperidone efficacy were found upstream of the GFRA2 gene, located on 8p21.3. Numerous studies in different populations have indicated a genetic association between schizophrenia and chromosome 8p, particularly in the 8p21 region. This schizophrenia susceptibility locus is referred to as SCZD6. Candidate genes in that region include neuregulin 1 (NRG1), adrenergic α-1A-receptor (ADRA1A), and frizzled homolog 3 (FZD3). The findings of the above study suggest adding GFRA2 to the list of genes in that region, which may play a role in schizophrenia and antipsychotic treatment. The GFRA2 protein is a cell surface receptor for GDNF and neurturin. Several studies have linked GDNF to schizophrenia. In an animal study in which PCP was injected into rats to produce schizophrenia-like symptoms, Semba et al. showed that PCP alters the function of GDNF in the ventral midbrain, where dopamine cell bodies are localized. The results above suggest that new studies should be undertaken to investigate the interplay of GDNF, neurturin, and GRFA2 in the etiology of schizophrenia and in the response to antipsychotic treatments.

Several SNPs identified in the above study lay in intergenic regions, sometimes far away from any known gene. One such SNP is rs4528226, which showed the most statistically significant association with change in PANSS-T in all analyses (Table 2, FIGS. 1 and 2f). This SNP is located approximately 200 kb upstream from the HTR7 gene. Interestingly, it has been shown that iloperidone has high affinity for the 5-HT, receptor. The biological relevance of SNPs located in intergenic DNA is currently difficult to assess. Although most genetic research has historically focused on coding sequences of genes and nearby promoter regions, comparative genomics studies are uncovering other functional genomic elements that can be located in introns and in gene-poor "desert" regions sometimes hundreds or thousands of kilobases away from the genes they regulate. It is possible that the intergenic SNPs examined in the above study are within regulatory elements, response elements, transposable elements, noncoding RNAs, coding sequences, or splicing sites that have not yet been identified. Alternatively, they may be in linkage disequilibrium with these elements or sequences. So far, no long-range cis-regulatory elements of HTR7 have been identified. The above results suggest that the genomic region of rs4528226 should be thoroughly examined for the presence of such elements.

The results of the WGAS offer the possibility of not only predicting an individual's response to treatment with iloperidone or an iloperidone metabolite, but of making such treatment more effective. For example, an individual predicted to respond well to treatment with iloperidone or an iloperidone metabolite, based on the individual's genotype at one or more SNP loci described above, may be administered a lower dosage (e.g., between about 2 mg/day and about 24 mg/day, between about 5 mg/day and about 20 mg/day, or between about 10 mg/day and about 15 mg/day) than would otherwise be administered, thereby minimizing the possibility of any adverse side effects of such treatment. Similarly, an individual predicted to not respond well to treatment with iloperidone or an iloperidone metabolite may be administered a higher dosage (e.g., between about 24 mg/day and about 50 mg/day, between about 30 mg/day and about 50 mg/day, or between about 40 mg/day and about 50 mg/day) or may be treated with another compound instead of or in addition to iloperidone or an iloperidone metabolite.

Alternatively, the dosage may be based on a patient's genotype at a particular SNP locus. For example, in one embodiment, the invention provides a method of treating a patient for one or more symptoms of a psychotic disorder, schizophrenia, or bipolar disorder, the method comprising: determining the patient's genotype in both copies of one single nucleotide polymorphism (SNP) locus selected from a group consisting of: rs11851892, rs9643483, rs875326, rs2513265, rs7837682, and rs4528226; and in the case that the patient has a genotype that is associated with iloperidone efficacy at the chosen SNP locus, administering to the patient an effective amount of an atypical antipsychotic based on the patient's rs11851892, rs9643483, rs875326, rs2513265, rs7837682, or rs4528226 genotype.

An individual's genotype at one or more of the SNP loci described above may be determined by any number of methods. For example, the genotype(s) may be determined by analyzing the DNA sequence directly, as described above. Alternatively, the genotype(s) may be determined by analyzing an RNA transcript (e.g., mRNA) or a gene expression product (e.g., a protein), as will be recognized by one skilled in the art. Genotyping is preferably performed ex vivo.

An additional aspect of the invention is a kit for determining treatment strategy for a patient with a psychotic disorder or bipolar disorder. Such kit is useful, e.g., in predicting a patient's response to treatment with an atypical antipsychotic, such as iloperidone, and, on the basis of such prognosis, treating the patient with a lower or higher dose of an atypical antipsychotic, treating the patient with an atypical antipsychotic in combination with other therapies, e.g., a typical antipsychotic, or choosing a different treatment altogether.

A kit of the invention is a combination of physical elements, e.g., probes, including without limitation specific primers, labeled nucleic acid probes, antibodies, protein-capture agent(s), reagent(s), instruction sheet(s) and other elements useful to practice the invention, in particular, to identify the alleles present in the genetic loci described herein.

A kit of the invention may include at least one reagent specific for detecting a patient's genotype at at least one of the relevant genetic loci, as described elsewhere herein. Detection can be direct, e.g., by directly sequencing the relevant portion of a person's chromosomal DNA, or indirect, e.g., by sequencing messenger RNA transcripts or by sequencing gene expression products, i.e., polypeptides. Thus, the reagent may be, e.g., a polynucleotide, or an array of polynucleotides, or an antibody or a panel of antibodies.

The kit may also comprise one or more gene specific genotyping primer composition. The primer composition can comprise at least one gene specific genotyping polynucleotide. The composition can comprise two or more sets of allele specific primer pairs. The two allele specific genotyping oligonucleotides may be packaged in separate containers. In some embodiments, degenerate primer sets are provided for amplification.

In another embodiment, the kit may optionally include instructions for isoelectric focusing methods for detecting and distinguishing gene expression products.

Antibody based kits can comprise, e.g., an antibody that is specific for the gene expression product of a given allele and that is bound to a solid support; and a second antibody that binds the gene expression product and that is conjugated to a detectable group.

The kit may also comprise reagents such as buffering agents, hybridization buffers, and protein or nucleic acid stabilizing agents, e.g., polysaccharides and the like. If carrying out the assay requires amplification of DNA or RNA, such as by PCR, then the kit may also comprise a polymerase or a reaction buffer. The kit may be packaged in any suitable manner, typically with all elements in a single container along with a sheet of printed instructions for carrying out the test or for interpreting results.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims

TABLE 1

Genotyping assays for selected SNPs in candidate genes

| Gene | dbSNP | Method | Temp. (° C.) | Enzyme | Allele 1 | Product (1) | Allele 2 | Product (2) |
|---|---|---|---|---|---|---|---|---|
| COMT | rs17850006 Val158Met | RFLP[2] | 61 | NlaIII | G | 114 + 36 + 35 | A | 96 + 36 + 35 + 18 |
| DRD2 | rs6275 His313 | RFLP | 63 | NcoI | C | 360 | T | 251 + 109 |
| DRD4 | rs12720389 521C/T | RFLP[2] | 60 | FspI | C | 562 + 42 | T | 384 + 219 |
| GRM3 | rs274622 | RFLP | 58 | Sau96I | C | 124 + 27 | T | 151 |
| HTR1A | Not available[1] C(1019)G | ASP[2] | 58 | NA | C | NA | G | NA |
| HTR2A | rs6341 T102C | RFLP[2] | 58 | HpaII | C | 216 + 126 | T | 342 |
| NOS1 | rs3782221 | ASP | 55 | NA | A | NA | G | NA |
| SYN2 | rs795009 | RFLP | 58 | Cac8I | A | 235 | C | 115 + 80 |
| SYN2 | rs308961 | ASP | 56 | NA | A | NA | C | NA |

Gene names correspond to the NCBI official symbols. SNPs are identified by their unique dbSNP number (http://www.ncbi.nlm.nih.gov/projects/SNP/), when available. Their common designation in the literature is indicated between parentheses below the dbSNP number. Primer sequences are from 5' to 3'; F and R refer to forward and reverse primers used in the PCR reaction, respectively (for ASP assays, 1 and 2 distinguish the allele-specific primers). PCR product size after complete enzymatic digestion is shown for each allele in base pairs.
[1]The SNP tested within the HTR1A gene was previously referred to as [C(-1019)G][14]; no dbSNP number is listed for this SNP.
[2]Primer sequences were previously reported by Hamajima et al,[12] Ronai et al,[13] Huang et al,[14] and Joober et al.[15]
RFLP, restriction fragment length polymorphism; ASP, allele-specific primer.

TABLE 2

SNPs significantly associated with PANSS-T in iloperidone-treated group

| SNP | dbSNP | Gene | Location | Position | Genotype |
|---|---|---|---|---|---|
| SNP_A-2048427 | rs11851892 | NPAS3 | 14q13.1 | 32921165 | non-GG |
| SNP_A-2283283 | rs9643483 | XKR4 | 8q12.1 | 55960228 | non-GG |
| SNP_A-1973093 | rs875326 | TNR | 1q25.1 | 172021056 | non-AG |
| SNP_A-2284243 | rs2513265 | GRIA4 | 11q22.3 | 104929005 | non-TT |
| SNP_A-2274533 | rs7837682 | GRFA2 | 8p21.3 | 21329990 | AA |
| SNP_A-2076797 | rs4528226 | NUDT9P1 | 10q23.31 | 92822226 | GT |

| | P | | | | | | Rank | | |
|---|---|---|---|---|---|---|---|---|---|
| SNP | Discovery | Confirmatory | BH-adjusted P | LOCF[1] | BH-adjusted P[1] | MMRM[2] | BH-adjusted P[2] | Discovery | Confirmatory | ANOVA LOCF | MMRM |
| SNP_A-2048427 | 0.000086 | 0.099 | 0.61 | 0.000028 | 0.86 | 0.000093 | 0.59 | 13 | 15 | 14 | 38 |
| SNP_A-2283283 | 0.00013 | 0.066 | 0.55 | 0.000055 | 0.86 | 0.00017 | 0.59 | 28 | 12 | 45 | 70 |
| SNP_A-1973093 | 0.00013 | 0.13 | 0.61 | 0.000040 | 0.86 | 0.000021 | 0.57 | 32 | 20 | 23 | 10 |
| SNP_A-2284243 | 0.00017 | 0.81 | 0.96 | 0.000042 | 0.86 | 0.000055 | 0.59 | 44 | 83 | 26 | 22 |

TABLE 2-continued

SNPs significantly associated with PANSS-T in iloperidone-treated group

| | | | | | | | | | | |
|---|---|---|---|---|---|---|---|---|---|---|
| SNP_A-2274533 | 0.00021 | 0.13 | 0.61 | 0.000077 | 0.86 | 0.00018 | 0.59 | 62 | 21 | 60 | 73 |
| SNP_A-2076797 | 0.00028 | 0.00041 | 0.041 | 0.00000011 | 0.12 | 0.00000078 | 0.26 | 76 | 1 | 1 | 1 |

SNPs are identified by their Affymetrix SNP nomenclature (SNP_A-) and their unique dbSNP number (http://www.ncbi.nlm.nih.gov/projects/SNP/). Each gene name corresponds to the National Center for Biotechnology Information (NCBI) official symbol of the gene closest to the SNP. The address of each SNP in the genome is indicated by the cytogenetic location and the physical position as listed in the NCBI Build 36.1, March 2006, as listed at http://www.ncbi.nlm.nih.gov/entrez/query.fcgi?db = snp. The genotype class associated with the better treatment response, as determined by the ANOVA test on LOCF data, is indicated. Allele designation refers to the Affymetrix annotation listed at http://www.ncbi.nlm.nih.gov/SNP/index.html. Rank refers to SNP in each analysis when ordered from lowest to highest P value. P values of the discovery phase were obtained from the truncated nonparametric measure ANOVA, based on the Kruskal-Wallis test with genotype as the grouping variable, using the LOCF data on the extremes of the distribution of 50% of the patients treated with iloperidone. P values of the confirmatory phase were obtained using independent group t tests of the change in PANSS-T on Day 28 LOCF data for patients in iloperidone Group 2, before and after correction for multiple testing (100 SNPs) using the FDR method (BH-adjusted P).
[1] ANOVA P values were obtained with LOCF data of all iloperidone-treated patients before and after correction for multiple testing (BH-adjusted P).
[2] P values of the MMRM analysis were obtained between genotype classes among all iloperidone-treated patients before and after correction for multiple testing (BH-adjusted P).

TABLE 3

Genotype effect on iloperidone and placebo response

| | | | Iloperidone | | | Placebo | | | |
|---|---|---|---|---|---|---|---|---|---|
| dbSNP | Gene | Genotype | N | Mean | SD | N | Mean | SD | |
| rs11851892 | NPAS3 | AA | 9 | −19.94 | 2.44 | 3 | −8.97 | 3.33 | |
| | | AG | 56 | −20.15 | 3.87 | 31 | −11.10 | 3.50 | |
| | | GG* | 145 | −9.20 | 4.25 | 63 | −5.90 | 4.00 | 0.20 |
| | | non-GG† | 65 | −20.12 | 3.69 | 34 | −10.91 | 3.49 | 0.0090 |
| P | | | | 0.000093 | | | 0.34 | | |
| rs9643483 | XKR4 | GG* | 47 | −3.30 | 3.93 | 20 | −11.21 | 3.77 | 0.12 |
| | | GT | 96 | −14.57 | 4.35 | 45 | −6.33 | 4.21 | |
| | | TT | 67 | −15.66 | 4.28 | 34 | −7.19 | 4.00 | |
| | | non-GG† | 163 | −15.02 | 4.34 | 79 | −6.70 | 4.12 | 0.00043 |
| P | | | | 0.00017 | | | 0.27 | | |
| rs875326 | TNR | AA | 25 | −14.99 | 4.27 | 10 | −6.75 | 5.32 | |
| | | AG* | 76 | −6.21 | 4.51 | 38 | −7.27 | 3.51 | 0.72 |
| | | GG | 105 | −16.73 | 4.33 | 49 | −7.81 | 4.40 | |
| | | non-AG† | 130 | −16.39 | 4.35 | 59 | −7.63 | 4.54 | 0.00061 |
| P | | | | 0.000021 | | | 0.98 | | |
| rs2513265 | GRIA4 | AA | 63 | −15.30 | 4.46 | 33 | −6.92 | 3.28 | |
| | | AT | 99 | −15.17 | 4.16 | 50 | −8.08 | 4.24 | |
| | | TT* | 48 | −3.30 | 4.11 | 15 | −4.84 | 4.03 | 0.86 |
| | | non-TT† | 162 | −15.22 | 4.26 | 83 | −7.62 | 3.91 | 0.0010 |
| P | | | | 0.000055 | | | 0.55 | | |
| rs7837682 | GRFA2 | AA† | 116 | −15.95 | 4.23 | 59 | −6.55 | 3.81 | 0.0011 |
| | | AG | 64 | −6.04 | 4.55 | 24 | −7.97 | 4.28 | |
| | | GG | 18 | −6.21 | 3.21 | 8 | −9.79 | 3.97 | |
| | | non-AA* | 82 | −6.08 | 4.28 | 32 | −8.43 | 4.22 | 0.50 |
| P | | | | 0.00018 | | | 0.58 | | |
| rs4528226 | NUDT9P1 | GG | 57 | −7.14 | 4.10 | 28 | −5.23 | 3.42 | |
| | | GT† | 99 | −18.73 | 3.99 | 42 | −11.68 | 3.96 | 0.016 |
| | | TT | 52 | −6.04 | 4.45 | 28 | −2.97 | 4.08 | |
| | | non-GT* | 109 | −6.61 | 4.29 | 56 | −4.10 | 3.90 | 0.36 |
| P | | | | 0.00000078 | | | 0.051 | | |

SNPs are identified by their unique dbSNP number (http://www.ncbi.nlm.nih.gov/projects/SNP/). Each gene name corresponds to the NCBI official symbol of the gene closest to the SNP. The two genotypes classes used in the MMRM analysis are indicated as associated with lowest response (*) or highest response (†) to iloperidone treatment. Allele designation refers to the Affymetrix annotation, as listed at http://www.ncbi.nlm.nih.gov/SNP/index.html. Number of patients (N), mean of change in PANSS-T (mean), and standard deviation (SD) of the mean shown are derived from the MMRM analysis. P values are shown for the two genotype classes used in the analysis within each group, with the corresponding means in bold. P values of the effect of the two genotype classes tested in the MMRM analysis between the iloperidone and placebo groups are shown.

TABLE 4

Odds ratios, sensitivity, specificity, and predictive values of SNPs associated with change in PANSS-T in iloperidone-treated patients

| | | | Improvement < 20% | | Improvement ≥ 20% | | Odds | | 95% Confidence | | | | |
|---|---|---|---|---|---|---|---|---|---|---|---|---|---|
| SNP | Gene | Genotype | −test | +test | −test | +test | Ratio | P | Interval | Sensitivity | Specificity | PV− | PV+ |
| rs11851892 | NPAS3 | non-GG | 87 | 23 | 58 | 42 | 2.74 | 0.0011 | 1.492-5.028 | 0.42 | 0.79 | 0.60 | 0.65 |
| rs9643483 | XKR4 | non-GG | 35 | 75 | 12 | 88 | 3.42 | 0.0009 | 1.658-7.062 | 0.88 | 0.32 | 0.74 | 0.54 |
| rs875326 | TNR | non-AG | 54 | 53 | 22 | 77 | 3.57 | <0.0001 | 1.944-6.542 | 0.78 | 0.50 | 0.71 | 0.59 |

TABLE 4-continued

Odds ratios, sensitivity, specificity, and predictive values of SNPs associated with change in PANSS-T in iloperidone-treated patients

| SNP | Gene | Genotype | Improvement < 20% −test | Improvement < 20% +test | Improvement ≥ 20% −test | Improvement ≥ 20% +test | Odds Ratio | P | 95% Confidence Interval | Sensitivity | Specificity | PV− | PV+ |
|---|---|---|---|---|---|---|---|---|---|---|---|---|---|
| rs2513265 | GRIA4 | non-TT | 33 | 77 | 15 | 85 | 2.43 | 0.011 | 1.225-4.811 | 0.85 | 0.30 | 0.69 | 0.52 |
| rs7837682 | GRFA2 | AA | 56 | 49 | 26 | 67 | 2.95 | 0.0004 | 1.627-5.33 | 0.72 | 0.53 | 0.68 | 0.58 |
| rs4528226 | NUDT9P1 | GT | 71 | 38 | 38 | 61 | 3.00 | 0.0001 | 1.705-5.277 | 0.62 | 0.65 | 0.65 | 0.62 |

SNPs are identified by their unique dbSNP number (http://www.ncbi.nlm.nih.gov/projects/SNP/). Each gene name corresponds to the NCBI official symbol of the gene closest to the SNP. The genotype class shown here is the genotype class associated with better efficacy with iloperidone treatment. Allele designation refers to the Affymetrix annotation listed at http://www.ncbi.nlm.nih.gov/SNP/index.html. The number of patients with improvement in PANSS-T above and below 20% is shown per genotype class. The percentage of improvement in PANSS-T was calculated from the LOCF data as 100*[Change from baseline/(baseline − number of items comprising the score)]. Genetic test results were defined as positive (+) for the genotype class associated with better response specified in the "genotype" column and as negative (−) for all other genotypes.
PV−, negative predictive value; PV+, positive predictive value.

What is claimed is:

1. A method comprising:
   determining an individual's genotype at a single nucleotide polymorphism (SNP) locus rs875326;
   in the case that the individual's genotype at the rs875326 SNP locus is non-AG: predicting that treating the individual with an atypical antipsychotic will be efficacious; and
   administering to the individual a dose of between about 2 mg/day and about 24 mg/day of iloperidone, a pharmaceutically-acceptable salt thereof, a metabolite thereof, or a pharmaceutically-acceptable salt of a metabolite thereof; and
   in the case that the individual's genotype at the rs875326 SNP locus is AG: predicting that treating the individual with an increased dose of an antipsychotic would be efficacious, wherein the increased dose is a greater dose than would be used to treat an individual with a non-AG genotype at the rs875326 SNP locus; and
   administering to the individual an increased close of between about 24 mg/day and about 50 mg/day of iloperidone, a pharmaceutically-acceptable salt thereof, a metabolite thereof, or a pharmaceutically-acceptable salt of a metabolite thereof.

2. The method of claim 1, wherein the iloperidone metabolite is selected from a group consisting of: 4-[3-[4-(6-Fluoro-1,2-benzisoxazol-3-yl)-1-piperidinyl]propoxy]-3-methoxy-α-methylbenzene methanol, 1-[4-[3-[4-(6-Fluoro-1,2-benzisoxazol-3-yl)-1-piperidinyl]propoxy]-3-hydroxyphenyl]ethanone, 1-[4-[3-[4-(6-Fluoro-1,2-benzisoxazol-3-yl)-1-piperidinyl]propoxy]-3-methoxyphenyl]-2-hydroxyethanone, 4-[3-[4-(6-Fluoro-1,2-benzisoxazol-3-yl)-1-piperidinyl]propoxy]-3-hydroxy-α-methylbenzene methanol, 4-[3-[4-(6-Fluoro-1,2-benzisoxazol-3-yl)-1-piperidinyl]propoxy]-2-hydroxy-5-methoxy-α-methylbenzene methanol, 1-[4-[3-[4-(6-Fluoro-1,2-benzisoxazol-3-yl)-1-piperidinyl]propoxy]-2-hydroxy-5-methoxyphenyl]ethanone, and 1-[4-[3-[4-(6-Fluoro-1,2-benzisoxazol-3-yl)-1-piperidinyl]propoxy]-2,5-dihydroxyphenyl]ethanone.

3. The method of claim 1, wherein the dose administered to the individual with a non-AG genotype is between about 5 mg/day and about 20 mg/day.

4. The method of claim 3, wherein the dose administered to the individual with a non-AG genotype is between about 10 mg/day and about 15 mg/day.

5. The method of claim 1, wherein the increased dose is between about 30 mg/day and about 50 mg/day.

6. The method of claim 5, wherein the increased dose is between about 40 mg/day and about 50 mg/day.

7. A method of treating a human patient for one or more symptoms of a psychotic disorder, the method comprising:
   determining the patient's genotype in both copies of the single nucleotide polymorphism (SNP) locus rs875326; and
   in the case that the individual's genotype at the rs875326 SNP locus is non-AG, administering to the patient a first effective amount of iloperidone, a pharmaceutically-acceptable salt thereof, a metabolite thereof, or a pharmaceutically-acceptable salt of a metabolite thereof, the first effective amount being between about 2 mg/day and about 24 mg/day; and
   in the case that the individual's genotype at the rs875326 SNP locus is AG, administering to the patient a second effective amount of iloperidone, a pharmaceutically-acceptable salt thereof, a metabolite thereof, or a pharmaceutically-acceptable salt of a metabolite thereof, the second effective amount being between about 24 mg/day and about 50 mg/day and greater than the first effective amount.

8. The method of claim 7, wherein the iloperidone metabolite is selected from a group consisting of: 4-[3-[4-(6-Fluoro-1,2-benzisoxazol-3-yl)-1-piperidinyl]propoxy]-3-methoxy-α-methylbenzene methanol, 1-[4-[3-[4-(6-Fluoro-1,2-benzisoxazol-3-yl)-1-piperidinyl]propoxy]-3-hydroxyphenyl]ethanone, 1-[4-[3-[4-(6-Fluoro-1,2-benzisoxazol-3-yl)-1-piperidinyl]propoxy]-3-methoxyphenyl]-2-hydroxyethanone, 4-[3-[4-(6-Fluoro-1,2-benzisoxazol-3-yl)-1-piperidinyl]propoxy]-3-hydroxy-α-methylbenzene methanol, 4-[3-[4-(6-Fluoro-1,2-benzisoxazol-3-yl)-1-piperidinyl]propoxy]-2-hydroxy-5-methoxy-α-methylbenzene methanol, 1-[4-[3-[4-(6-Fluoro-1,2-benzisoxazol-3-yl)-1-piperidinyl]propoxy]-2-hydroxy-5-methoxyphenyl]ethanone, and 1-[4-[3-[4-(6-Fluoro-1,2-benzisoxazol-3-yl)-1-piperidinyl]propoxy]-2,5-dihydroxyphenyl]ethanone.

9. The method of claim 7, wherein the first effective amount is between about 5 mg/day and about 20 mg/day.

10. The method of claim 9, wherein the first effective amount is between about 10 mg/day and about 15 mg/day.

11. The method of claim 7, wherein the second effective amount is between about 30 mg/day and about 50 mg/day.

12. The method of claim 11, wherein the second effective amount is between about 40 mg/day and about 50 mg/day.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: primer sequence

<400> SEQUENCE: 1
catgcagcta tgtttgggag					20

<210> SEQ ID NO 2
<211> LENGTH: 22
<212> TYPE: DNA
<213> ORGANISM: Artificial Sequence
<220> FEATURE:
<223> OTHER INFORMATION: primer sequence

<400> SEQUENCE: 2
gccaaaataa tgtgtagcaa tc				22

<210> SEQ ID NO 3
<211> LENGTH: 22
<212> TYPE: DNA
<213> ORGANISM: Artificial Sequence
<220> FEATURE:
<223> OTHER INFORMATION: primer sequence

<400> SEQUENCE: 3
gattggcttt gggtttgcct tg				22

<210> SEQ ID NO 4
<211> LENGTH: 20
<212> TYPE: DNA
<213> ORGANISM: Artificial Sequence
<220> FEATURE:
<223> OTHER INFORMATION: primer sequence

<400> SEQUENCE: 4
gaccccatct ttagcggaac					20

<210> SEQ ID NO 5
<211> LENGTH: 20
<212> TYPE: DNA
<213> ORGANISM: Artificial Sequence
<220> FEATURE:
<223> OTHER INFORMATION: primer sequence

<400> SEQUENCE: 5
gaagggtcta cctcgattcc                                               20

<210> SEQ ID NO 6
<211> LENGTH: 20
<212> TYPE: DNA
<213> ORGANISM: Artificial Sequence
<220> FEATURE:
<223> OTHER INFORMATION: primer sequence

<400> SEQUENCE: 6
gatcagctta ttcaaccctc                                               20

<210> SEQ ID NO 7
<211> LENGTH: 22
<212> TYPE: DNA
<213> ORGANISM: Artificial Sequence
<220> FEATURE:
<223> OTHER INFORMATION: primer sequence

<400> SEQUENCE: 7
ctaaaggcga acatgtgta tg                                             22

<210> SEQ ID NO 8
<211> LENGTH: 22
<212> TYPE: DNA
<213> ORGANISM: Artificial Sequence
<220> FEATURE:
<223> OTHER INFORMATION: primer sequence

<400> SEQUENCE: 8
catagcagct gaccaacatt cc                                            22

<210> SEQ ID NO 9
<211> LENGTH: 22
<212> TYPE: DNA
<213> ORGANISM: Artificial Sequence
<220> FEATURE:
<223> OTHER INFORMATION: primer sequence

<400> SEQUENCE: 9
caatctgctt tcacctcaac cc                                            22

<210> SEQ ID NO 10
<211> LENGTH: 20
<212> TYPE: DNA
<213> ORGANISM: Artificial Sequence
<220> FEATURE:
<223> OTHER INFORMATION: primer sequence

<400> SEQUENCE: 10
ctgccaccct actcaacacc                                               20

<210> SEQ ID NO 11
<211> LENGTH: 20
<212> TYPE: DNA
<213> ORGANISM: Artificial Sequence
<220> FEATURE:
<223> OTHER INFORMATION: primer sequence

<400> SEQUENCE: 11
gagcagataa atttgcctgg                                               20

<210> SEQ ID NO 12
<211> LENGTH: 22
<212> TYPE: DNA

```
<213> ORGANISM: Artificial Sequence
<220> FEATURE:
<223> OTHER INFORMATION: primer sequence

<400> SEQUENCE: 12
gttgaaccca aagacacccc tg                                              22
```